United States Patent

Gasc et al.

[11] Patent Number: 5,064,853
[45] Date of Patent: Nov. 12, 1991

[54] 4(2-INDOLYL)2-AMINO-PENTANEDIOIC ACIDS AND CHOLECYOSTOKININ USE THEREOF

[75] Inventors: Jean-Claude Gasc, Bondy; Daniel Humbert, Fontenay sous Bois; Mario Vekens, Courbevoie, all of France

[73] Assignee: Roussel Uclaf, Paris, France

[21] Appl. No.: 478,479

[22] Filed: Feb. 12, 1990

[30] Foreign Application Priority Data

Feb. 17, 1989 [FR] France ................. 89 02093

[51] Int. Cl.$^5$ .................. A61K 31/405; C07D 209/12
[52] U.S. Cl. ................... 514/419; 548/492; 548/494
[58] Field of Search ................. 548/494; 514/419

[56] References Cited

U.S. PATENT DOCUMENTS 4,000,692 6/1989 Floyd et al. ................. 598/492
4,965,369 10/1990 Maetzel et al. ............... 548/492

*Primary Examiner*—David B. Springer
*Attorney, Agent, or Firm*—Bierman and Muserlian

[57] ABSTRACT

All possible isomeric forms and mixtures thereof of compounds of the formula

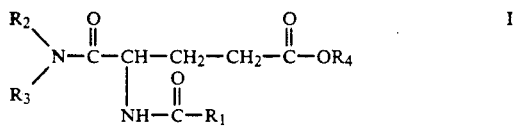

wherein $R_1$ is selected from the group consisting of indolyl, pyridyl, piperidinyl, quinolyl, thiazolyl and aryl of 6 to 14 carbon atoms and aralkyl of 7 to 18 carbon atoms with the latter two being unsubstituted or substituted with at least one member of the group consisting of halogen, alkyl and alkoxy of 1 to 8 carbon atoms, dialkylamino with alkyls of 1 to 8 carbon atoms, $-CF_3$, $-CN$ and $-NO_2$, $R_2$ is selected from the group consisting of

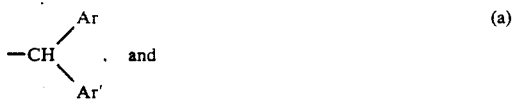

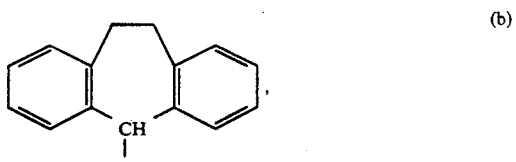

$Ar'$ are selected from the group consisting of pyridyl, indolyl, thiazolyl and aryl of 6 to 14 carbon atoms with the latter and the phenyl ring of b) being substituted or substituted with at least one member of the group consisting of halogen, alkyl and alkoxy of 1 to 8 carbon atoms, dialkylamino with alkyls of 1 to 8 carbon atoms, $-CF_3$, $-CN$ and $-NO_2$ and $R_3$ is hydrogen or $R_2$ and $R_3$ together with the nitrogen to which they are attached form a 5 to 7 member hydrocarbyl ring optionally containing an oxygen or a second nitrogen unsubstituted or substituted with at least one member of the group consisting of alkyl of 1 to 8 carbon atoms, aryl of 6 to 14 carbon atoms and

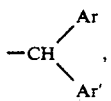

Ar and Ar' having the above definitions and $R_4$ is selected from the group consisting of hydrogen, alkyl of 1 to 8 carbon atoms, cycloalkyl of 3 to 8 carbon atoms,

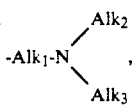

and aralkyl of 7 18 carbon atoms unsubstituted or substituted with at least one member of the group consisting of halogen, alkyl and alkoxy of 1 to 8 carbon atoms, dialkylamino with alkyls of 1 to 8 carbon atoms, $-CF_3$, $-CN$ and $-NO_2$, $Alk_1$ is an alkylene of 2 to 8 carbon atoms and $alk_2$ and $Alk_3$ are individually alkyl of 1 to 8 carbon atoms or cycloalkyl of 3 to 8 carbon atoms having cholecystokinin agonistic or antagonistic activity.

15 Claims, No Drawings

4(2-INDOLYL)2-AMINO-PENTANEDIOIC ACIDS AND CHOLECYOSTOKININ USE THEREOF

STATE OF THE ART

Related prior art includes U.S. Pat. No. 4,791,215, British application No. 2,160,869 and Eur. J. Med. Chim. Ther., Vol. 21, No. 1 (1986), p. 9 to 20.

OBJECTS OF THE INVENTION

It is an object of the invention to provide the novel compounds of formula I and a novel process and novel intermediates for their preparation.

It is another object of the invention to provide novel cholecystokinin agonistic compositions and a novel method of inducing cholecystokinin agonistic activity in warm-blooded animals.

These and other objects and advantages of the invention will become obvious from the following detailed description.

THE INVENTION

The novel compounds of the invention are All possible isomeric forms and mixtures thereof of compounds of the formula

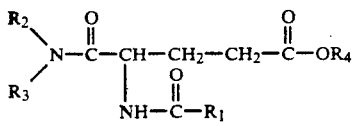

wherein $R_1$ is selected from the group consisting of indolyl, pyridyl, piperidinyl, quinolyl, thiazolyl and aryl of 6 to 14 carbon atoms and aralkyl of 7 to 18 carbon atoms with the latter two being unsubstituted or substituted with at least one member of the group consisting of halogen, alkyl and alkoxy of 1 to 8 carbon atoms, dialkylamino with alkyls of 1 to 8 carbon atoms, $-CF_3$, $-CN$ and $-NO_2$, $R_2$ is selected from the group consisting of

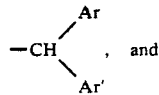, and

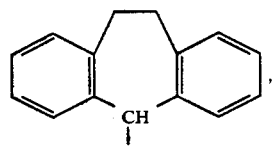

Ar and Ar' are selected from the group consisting of pyridyl, indolyl, thiazolyl and aryl of 6 to 14 carbon atoms with the latter and the phenyl ring of b) being unsubstituted or substituted with at least one member of the group consisting of halogen, alkyl and alkoxy of 1 to 8 carbon atoms, dialkylamino with alkyls of 1 to 8 carbon atoms, $-CF_3$, $-CN$ and $-NO_2$ and $R_3$ is hydrogen or $R_2$ and $R_3$ together with the nitrogen to which they are attached form a 5 to 7 member hydrocarbonyl ring optionally containing on oxygen or a second nitrogen unsubstituted or substituted with at least one member of the group consisting of alkyl of 1 to 8 carbon atoms, aryl of 6 to 14 carbon atoms and

Ar and Ar' having the above definitions and $R_4$ is selected from the group consisting of hydrogen, alkyl of 1 to 8 carbon atoms, cycloalkyl of 3 to 8 carbon atoms,

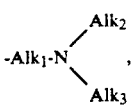

and aralkyl of 7 18 carbon atoms unsubstituted or substituted with at least one member of the group consisting of halogen, alkyl and alkoxy of 1 to 8 carbon atoms, dialkylamino with alkyls of 1 to 8 carbon atoms, $-CF_3$, $-CN$ and $-NO_2$, $Alk_1$ is an alkylene of 2 to 8 carbon atoms and $Alk_2$ and $Alk_3$ are individually alkyl of 1 to 8 carbon atoms or cycloalkyl of 3 to 8 carbon atoms.

Since the compounds of the invention possess one or more asymmetric carbon atoms, they can exist in racemic or enantiomeric form and they all possess an asymmetric carbon in position 4, and may also possess other asymmetric carbons according to the values of the substituents.

$R_1$ is preferably aryl or aralkyl such as phenyl optionally substituted with at least one member of the group consisting of halogen such as chlorine or bromine, alkyl of 1 to 5 carbon atoms such as methyl, ethyl, isopropyl or n-propyl, alkoxy of 1 to 5 carbon atoms such as methoxy, ethoxy, isopropoxyl or a dialkylamino such as dimethylamino or diethylamino. Examples of aralkyl are benzyl, phenethyl, 3-phenylpropyl and cinnamyl substituted with the above substitutents. Ar and Ar' are preferably phenyl optionally substituted as above.

When $R_2$ and $R_3$ form, together with the nitrogen atom to which they are linked, a carbonated ring, it is preferably

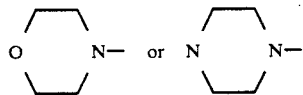

optionally substituted and more preferably the radicals:

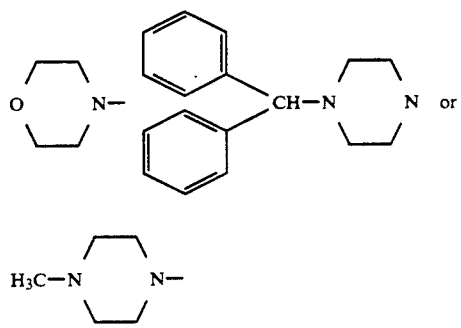

When $R_4$ is alkyl it is preferably methyl, ethyl, n-propyl, isopropyl or n-butyl. When $R_4$ is aralkyl it is preferably an optionally substituted benzyl. When $R_4$ is

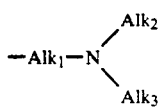

it is

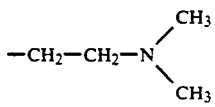

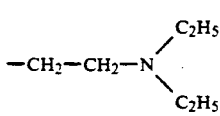

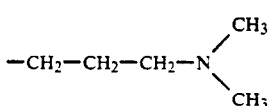

or:

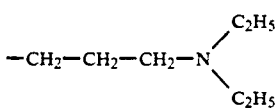

Among the preferred compounds of the invention are those of formula I wherein $R_1$ is indolyl, those wherein $R_2$ is

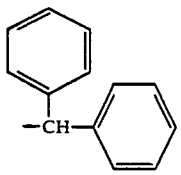

in which the phenyls are optionally substituted by at least one of the substituents given above for $R_1$, and especially the compounds in which $R_2$ is

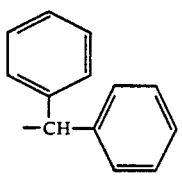 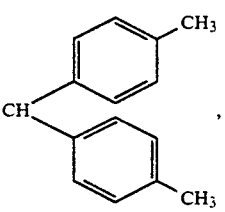,

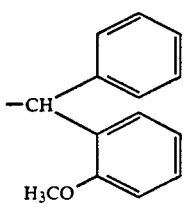 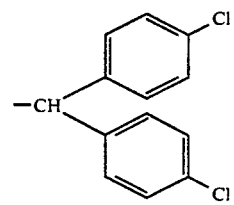

those wherein $R_2$ is

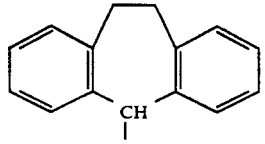

and those wherein $R_4$ is hydrogen. Among the preferred compounds of the invention are the compounds of S configuration at the carbon in position 4.

Specific preferred compounds of the invention are those of Examples 2, 4, 9 and 13.

The novel process of the invention for the preparation of compounds of formula I comprises reacting a compound of the formula

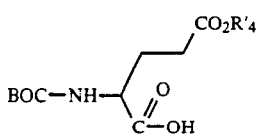 II wherein BOC is (1,1-dimethylethoxy)-carbonyl and $R_4'$ has the same meaning as $R_4$ with the exception of hydrogen with a compound of the formula

 III wherein $R_2$ and $R_3$ have the above definition to obtain the compound of the formula

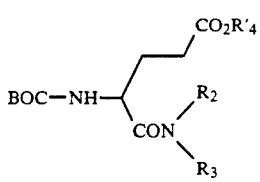 IV subjecting the latter to a deblocking agent of the amine function and reacting the resulting product with an acid or a derivative of an acid of the formula $R_1CO_2H$  V wherein $R_1$ has the above definition to obtain the compound of the formula

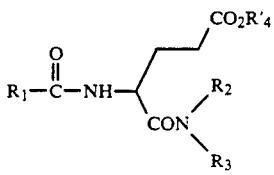 $I_A$ which is optionally reacted with a cleavage agent of the acid function to obtain the compound of the formula

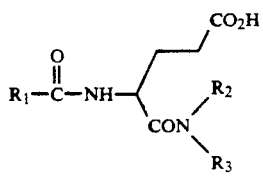

In a preferred method of carrying out the process of the invention, the compound of formula III is in the form of a salt, for example the hydrochloride and in the compound of formula II, $R_4'$ is benzyl.

The deblocking agent of the amine function is a strong acid such as hydrochloric acid or trifluoroacetic acid, and the operation is carried out in an organic solvent such as methylene chloride or ethyl acetate. The acid of formula V is used in the form of the acid, acid chloride or acid anhydride and the deblocking agent of the acid function is hydrogen in the presence of palladium or a base such as sodium hydroxide, potassium hydroxide, potassium carbonate, lithium hydroxide and the operation is preferably carried out in a solvent such as ethanol, dioxane, tetrahydrofuran, methanol, or dimethylformamide at a temperature between about 0° C. and the reflux temperature of the solvent used.

In a variation of the process, a compound of the formula

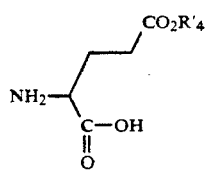

wherein $R_4'$ has the above definition is reacted with an acid or a derivative of an acid of formula V to obtain the compound of the formula

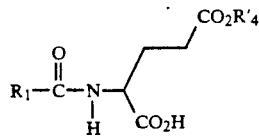

which is reacted with a compound of the formula

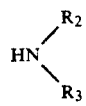

in which $R_2$ and $R_3$ have the above definition to obtain the corresponding compound of formula $I_A$ which is optionally subjected, to the action of a cleavage agent of the acid function to obtain the compound of formula $I_B$, $I_A$ or $I_B$ being defined as previously.

In a preferred method of carrying out the latter of the invention, the acid of formula V is in the form of the acid chloride and in the compound of formula VI, $R_4'$ is benzyl.

The products of formula IV and VII of the invention are new products and are themselves a subject of the present invention.

The cholecystokinin agonistic or antagonistic compositions of the invention are comprised of cholecystokinin agonistically or antagonistically effective amount of at least one compound of formula I and an inert pharmaceutical carrier. The compositions may be in the form of tablets, dragees, capsules, granules, suppositories and injectable solutions or suspensions.

Examples of suitable excipients are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives.

The compositions are agonists or antagonists of cholecystokinin, the bonding sites of which were made known at the central and peripheral level. Cholecystokinin is a peptide distributed widely in the brain, particularly in the cortex, the striatum, the hippocampus, the ventral tegmentum, the septum and the hypothalamus. Cholecystokinin is also secreted at a peripheral level by the small intestine and its action is shown notably by the stimulation of vesicular contraction, an increase in biliary secretion, control of pancreatic enzyme secretion, an action on gastric contractions, an action on intestinal motility. It might act in certain cases on arterial pressure and influence the immune systems.

Cholecystokinin co-exists in certain central neurones with dopamine and it also intervenes in mechanisms involving acetyl choline, GABA, serotonin, opioids, somatostatin, the substance P and ionic canals. Its administration causes physiological modifications: palpebral ptosis, hypothermia, hyperglycemia, catalepsy and behavioral modifications: hypolocomotricity, decrease in exploration, analgesia, action in learning, modification of sexual behavior and satiety. Depending on the doses, it behaves as a dopaminergic agonist or antagonist.

The compositions are useful in the treatment of certain intestinal disorders, of obesity, of behavioral, emotional, sexual and mnesic disorders, of schizophrenia and of various gastrointestinal disorders.

The novel method of the invention of inducing cholecystokinin agonistic or antagonistic activity in warm-blooded animals, including humans, comprising administering to warm-blooded animals a cholecystokinin agontistically or antagonistically effective amount of at least one compound of formula I. The compounds may be administered orally, rectally or parenterally and the usual daily dose is 0.00066 to 1.33 mg/kg depending on the condition treated, the specific compound and the method of administration.

In the following examples there are described several preferred embodiments to illustrate the invention. However, it is to be understood that the invention is not intended to be limited to the specific embodiments.

EXAMPLE 1

(±) 4-[benzoyl-amino]-5-[(diphenylmethyl)-amino]-5-oxo-pentanoic acid

STEP A: (±) 4-[[(1,1-dimethylethoxy)-carbonyl]-amino]-5-(diphenylmethyl)-amino]-5-oxo pentanoic acid To a suspension of 17.62 g of α-phenyl benzenemethanamine hydrochloride, 24.5 g of benzyl N-[(1,1-dimethylethoxy)-carbonyl]-L-5-glutamate, 10.5 g of N-hydroxybenzotriazole, 30.7 g of 1-[3-(dimethylamino)-propyl]-3-ethyl-carbodiimide hydrochloride and 350 ml of methylene chloride, 20.45 ml of N-ethylmorpholine were added dropwise with stirring at 5° C. and the mixture was stirred at room temperature for 18 hours. The reaction mixture was washed successively with 200 ml of hydrochloric acid, 200 ml of a 1N solution of sodium carbonate and 100 ml of water and the organic phase was dried over magnesium sulfate and the solvent was concentrated to obtain 36.3 g of the expected product as a white solid melting at 128° C. (90.2% yield).

STEP B: Benzyl (±) 4-amino-5-[(diphenylmethyl)-amino]-5-oxo-pentanoate 36.3 g of the product of Step A were dissolved in 700 ml of ethyl acetate and after cooling the solution to 5° C. in an ice bath, a current of hydrogen chloride was passed through the solution for one hour. The solvent was eliminated under reduced pressure and the residue was taken up in 500 ml of ethyl ether. The product was filtered to obtain 30.8 g of the expected hydrochloride melting at 105° C. (97.4% yield).

STEP C: Benzyl (±) 4-[(benzoyl)-amino]-5-[(diphenylmethyl)-amino]-5-oxo pentanoate To a suspension of 2 g of the hydrochloride of Step B, 0.55 g of benzoic acid, 0.91 g of hydroxy benzotriazole hydrate, 1.72 g of 1-[3-(dimethylamino)-propyl]-3-ethyl carbodiimide hydrochloride, and 20 ml of methylene chloride, 1.7 ml of N-ethylmorpholine were added dropwise with stirring at 5° C. and the resulting mixture was allowed to return to ambient temperature and was stirred for 18 hours. The organic phase was washed successively with 10 ml of N hydrochloric acid, 10 ml of a normal solution of sodium carbonate and twice with 10 ml of water. After drying over magnesium sulfate, the solvent was eliminated to obtain 2.4 g of the product as a yellowish solid melting at 115° C. (93.8% yield).

STEP D: (±) 4-[(benzoyl)-amino]-5-[(diphenylmethyl)-amino]-5-oxo pentanoic acid 2.1 g of the benzyl ester of Step C were hydrogenated in the presence of 500 mg of 10% palladized charcoal in a mixture of 50 ml of ethanol and 10 ml of acetic acid and after absorption of the desired quantity of hydrogen, the catalyst was filtered off. The solvents were eliminated under reduced pressure and the residue obtained was taken up in 50 ml of ether to obtain the product as a white solid melting at 118° C.

EXAMPLE 2

(S)-4-[[(1H-indol-2-yl)-carbonyl]-amino]-5-[[bis-(4-methylphenyl)-methyl]-amino]-5-oxo pentanoic acid STEP A: 5-benzyl (S)-2-[[(1H-indol-2-yl)-carbonyl]-amino]-pentanedioate acid 4.27 g of benzyl L-5-glutamate were suspended under nitrogen in 50 ml of acetone and then 22.5 mmoles of sodium carbonate were added in the form of a 1N solution in water. After stirring for half an hour and then cooling to 5° to 10° C., a solution of 2.9 g of 1H-indol-2-carboxylic acid chloride in 50 ml of acetone was added dropwise. At the end of the addition, the mixture was allowed to return to ambient temperature and was stirred overnight. It was poured into 200 ml of water and then acidified with concentrated hydrochloric acid. Extraction was done with ethyl acetate and the organic phase was washed with a saturated solution of sodium chloride, then dried over magnesium sulfate. The solvent was eliminated under reduced pressure and the oily residue was purified by chromatography on silica, then recrystallized from ether to obtain 6.7 g of the product as a beige solid melting at 144° C.

STEP B: Benzyl (S)-4-[[(1H-indol-2-yl)-carbonyl]-amino]-5-[[bis-(4-methylphenyl)-methyl]-amino]-5-oxo pentanoate 1.9 g of the product of Step A, 100 ml of methylene chloride, 1.01 g of hydroxy benzotriazole hydrate, 1.42 g of 1-[3-(dimethylamino)-propyl]-3-ethyl carbodiimide hydrochoride and 1.06 g of bis-4,4-dimethyl-benzhydrylamine were introduced successively. The mixture was stirred overnight and then was washed with one volume of 1N hydrochloric acid, one volume of a saturated solution of sodium bicarbonate and one volume of water. After drying the organic phase over magnesium sulfate and filtering, the solvent was eliminated under reduced pressure to obtain 2.6 g of the product melting at 146°≃150° C.

STEP C: (S)-4-[[(1H-indol-2-yl)-carbonyl]-amino]-5-[[bis-(4-methylphenyl)-methyl]-amino]-5-oxo pentanoic acid A current of hydrogen in the presence of 500 mg of palladium on 10% activated charcoal was passed through a solution containing 2.56 g of the product of Step B, 250 ml of absolute ethanol and 5 ml of acetic acid. The catalyst was filtered off and the solvent was eliminated. The residue was crystallized from ethanol to obtain 2.2 g of the product melting at >260° C.

EXAMPLE 3

Using the procedure of Example 1, the benzyl ester of (S)-5-[[bis-(4-chlorophenyl)-methyl]-amino]-5-oxo-4-[[(1H-indol-2-yl)-carbonyl]-amino]-pentanoic acid melting at 207° C. was obtained.

EXAMPLE 4

(S)-5-[[bis-(4-chlorophenyl)-methyl]-amino]-5-oxo-4-[[(1H-indol-2-yl)-carbonyl]-amino]-pentanoic acid 2.1 g of the benzyl ester of (S)-5-[[bis-(4-chlorophenyl)-methyl]-amino]-5-oxo-4-[[(1H-indol-2-yl)-carbonyl]-amino]-pentanoic acid were added at 5° C. to 10° C. to 30 ml of 90% ethanol and the suspension was admixed with 6.8 ml of 1N sodium hydroxide. The mixture was allowed to return to ambient temperature and was stirred for 16 hours. The light insoluble portion was filtered off and the solvent was eliminated. The residue was taken up in 20 ml of water and the solution was cooled to 0° C. to 5° C. and acidified with concentrated hydrochloric acid. A colorless precipitate was obtained which was filtered and washed with water and dried under reduced pressure to obtain 1.6 g of the desired product as a colorless solid (89.7% yield).

The compound was crystallized from a mixture of methanol and chloroform and after filtration, colorless crystals were obtained melting at >260° C. with a specific rotation of $[\alpha]_D = +0.967°$ C. (c=1.55% in dimethylformamide).

Analysis:
Calculated: % C. 61.84; % H 4.42; % N 8.01; % Cl 13.52
Found: 61.8; 4.3; 8.0; 13.5

Using the procedure of Example 1, the following products were obtained:

EXAMPLE 5

5-[(diphenylmethyl)-amino]-4-[[(1H-indol-2-yl)-carbonyl]-amino]-5-oxo pentanoic acid melting at 258°≃60° C.

EXAMPLE 6

Benzyl (S)-4-[[(1H-indol-2-yl)-carbonyl]-amino]-5-[[bis-(4-methoxyphenyl)-methyl]-amino]-5-oxo pentanoate melting at 187° C.

EXAMPLE 7

(S)-4-[[(1H-indol-2-yl)-carbonyl]-amino]-5-[[bis-(4-methoxyphenyl)-methyl]-amino-5-oxo pentanoic acid melting at 157° C.

EXAMPLE 8

Benzyl (4S)-4-[[(1H-indol-2-yl)-carbonyl]-amino]-5-[[(2-methoxyphenyl)-phenylmethyl]-amino]-5-oxo pentanoate melting at 148° C.

EXAMPLE 9

(4S)-4-[[(1H-indol-2-yl)-carbonyl]-amino]-5-[[(2-methoxyphenyl)-benzyl]-amino]-5-oxo pentanoic acid melting at 228° C.

EXAMPLE 10

Benzyl (S)-4-[(3,4-dichloro-benzoyl)-amino]-5-[(diphenylmethyl)-amino]-5-oxo pentanoate melting at 164° C.

EXAMPLE 11

(S)-4-[(3,4-dichloro benzoyl)-amino]-5-[(diphenylmethyl)-amino]-5-oxo pentanoic acid melting at 204° C.

EXAMPLE 12

(S)-5-[(diphenylmethyl)-amino]-4-[[(1H-indol-3-yl)-carbonyl]-amino]-5-oxo pentanoic acid melting at 141° C. The product was prepared starting from the corresponding benzyl ester melting at 190° C.

EXAMPLE 13

(S)-5-[(10,11-dihydro-dibenzo-[a,d]-cyclohepten-5-yl)-amino]-4-[[(1H-indol-2-yl)-carbonyl]-amino]-5-oxo pentanoic acid melting at >260° C. The product was prepared starting from the corresponding benzyl ester melting at 170°≃200° C.

EXAMPLE 14

(S)-5-[(diphenylmethyl)-amino]-4-[[(1H-indol-2-yl)-carbonyl]-amino]-5-oxo pentanoic acid melting at ≃200° C. The product was prepared starting from the corresponding benzyl ester melting at 168° C.

EXAMPLE 15

(S)-4-[(4-bromo-benzyl)-amino]-5-[(diphenylmethyl)-amino]-5-oxo pentanoic acid melting at 215° C. The product was prepared starting from the corresponding benzyl ester melting at 150° C.

EXAMPLE 16

(S)-5-[(diphenylmethyl)-amino]-5-oxo-4-[[(3-pyridyl)-carbonyl]-amino]- pentanoic acid melting at 220° C. The product was prepared starting from the corresponding benzyl ester melting at about 100° C.

EXAMPLE 17

(S)-5-[(diphenylmethyl)-amino]-4-[(4-methoxybenzoyl)-amino]-5-oxo pentanoic acid melting at 161° C. The product was prepared starting from the corresponding benzyl ester melting at 158° C.

EXAMPLE 18

(S)-5-[(diphenylmethyl)-amino]-5-oxo-4-[[(3-quinolyl)-carbonyl]-amino] pentanoic acid melting at 240° C. The product was prepared starting from the corresponding benzyl ester melting at 240° C.

EXAMPLE 19

(S)-5-[(diphenylmethyl)-amino]-4-[(4-nitro benzyl)-amino]-5-oxo] pentanoic acid melting at 219° C. The product was prepared starting from the corresponding benzyl ester melting at 137° C.

EXAMPLE 20

(4S)-5-[(diphenylmethyl)-amino]-5-oxo-4-[[(3-piperidinyl)-carbonyl[-amino] pentanoic acid melting at 166° C.

EXAMPLE 21

(S)-4-[[(1H-indol-2-yl)-carbonyl]-amino]-5-oxo-5-(1-piperazinyl) pentanoic acid.

EXAMPLE 22

(S)-5-[4-(diphenylmethyl)-1-piperazinyl]-4-[[(1H-indol-2-yl)-carbonyl]-amino]-5-oxo pentanoic acid.

EXAMPLE 23

(4S)-4-[[(1H-indol-2-yl)-carbonyl]-amino]-5-oxo-5-[phenyl-(3-pyridyl)-methyl]-amino] pentanoic acid.

EXAMPLE 24

2-(dimethylamino)-ethyl (S)-5-[(diphenylmethyl)-amino]-4-[[(1H-indol-2-yl)-carbonyl]-amino]-5-oxo pentanoate.

EXAMPLE 25

Tablets were prepared containing 20 ml of the product of Example 2 and sufficient excipient of lactose, wheat starch, treated starch, rice starch, magnesium stearate and talc for a tablet weight of 300 mg.

EXAMPLE 26

Capsules were prepared containing 50 mg of the product of Example 9 and sufficient excipient talc, magnesium stearate and aerosil q.s. for a capsule of 300 mg.

BIOLOGICAL STUDY

1) Central receptors

The cortices of 20 male rats weighing 150 to 200 g were removed and were ground up with a Polytron in 0.32M sucrose. After centrifuging, the supernatant was collected and centrifuged. The residue was suspended in 120 ml of Hepes buffer, pH 7.4, (Hepes 10 mM, NaCl 130 mM, $MgCl_2$, $6H_2O$ 5 mM, bacitracine 250 mg/liter, PMSF 1 mg/liter), and re-centrifuged. The residue was taken up in 120 ml of Hepes buffer pH 7.4, and recentrifuged at 30,000 g for 30 minutes. The residue was then taken up in 500 ml of Hepes buffer pH 7.4, which enabled 240 aliquots of 2 ml of homogenate to be obtained. The incubation was carried out at 25° C. for 30 minutes in the presence of 0.5 nM of 3H CCK8 and the product to be tested (10,000 micromoles for 1 dose, or with a range of 7 doses) or cold CCK8 ($10^{-6}M$), which was the reference product. After the homogenate aliquots were returned to 0° C., they were filtered with Whatman GF/B filters and the filtrates were washed with 3×5 ml of a Tris HCl 50 mM buffer, pH 7.4. The results are expressed in IC$_{50}$: concentration necessary to inhibit the fixed specific radioactivity by 50% in the Table below.

2) Peripheral receptors

The pancreases of 3 male rats weighing 150-200 g were removed and ground with a Polytron (4 grindings, speed 3, with an interval of 10 seconds between grindings) and the homogenate was filtered over a gauze, then centrifuged at 30,000 g for 30 minutes. The residue obtained was taken up in 400 volumes ($\simeq$600 ml) of Tris 50 mM HCl buffer, pH 7.4, containing 2 g/liter of BSA, 0.1 mM of bacitracin, 5 mM of MgCl$_2$ and 5 mM of dithiothreitol. 2 ml of homogenate aliquots were incubated at 25° C. for 60 minutes in the presence of 0.2 mM 3H CCK8 and the product to be tested (10,000 micromoles for 1 dose or with a range of 7 doses) and cold CCK8 ($10^{-6}$M) which was the reference product. After returning to 0° C., the aliquots were filtered with Whatman GF/B filters having been previously washed in a 0.05% solution of polyethyleneimine. The filtrate was washed with 3×5 ml of Tris HCl 50 mM buffer, pH 7.4. The results are expressed in IC$_{50}$: concentration necessary to inhibit the fixed specific radioactivity by 50%. (IC$_{50}$ in nanomoles).

| Action on the alimentary intake of a rat | | |
|---|---|---|
| | Peripheral CCK | Central CCK |
| Example 2 | 53 | 700 |
| Example 4 | 96 | 10000 |
| Example 9 | 32 | 682 |
| Example 13 | 1660 | 2660 |

The tests were carried out on groups of 5 rats weighing 250±10 g under the following conditions: the animals were placed individually in cages having a feeding trough described by FREGLY (J. Appln. Physiol., 1960, Vol. 15, p. 539) which had the advantage of avoiding the wastage of food presented when using powdered fodder. The rats were accustomed to taking their daily ration over 5 consecutive hours, drinking water being offered ad libitum. The amounts of food ingested were determined individually by weighing the feeding troughs and the consumptions were monitored every hour for 5 hours after the administration of 10 mg/kg of the compound intra-peritoneally. The amounts consumed were expressed in g/100 g of body weight per hour and the averages were compared with those obtained from the control animals by a DUNNET test. At a dose of 10 mg/kg intra-peritoneally, the product of Example 9 showed an anorexigenic activity and it significantly reduced by more than 50% the alimentary consumption of the treated animals relative to that of the control animals. At this dose, the product of Example 2 reduced the alimentary consumption by 15% which was not statitically significant.

Action on Guinea Pig's Isolated Ileum

The test was carried out on ileum fragments of male guinea pigs placed under a tension of 1 g in a Krebs solution aerated with carbogen and maintained at 37° C. The contractions were recorded using a micro-dynamometer connected to a polygraph. The ileum was left at rest for 30 minutes and then CCK8 was added to the bath at a concentration of 1×$10^{-8}$M. After rinsing, the product to be studied was added to the bath and left in contact with the organ for one minute. Then, CCK8 (1×$10^{-8}$M) was added to the bath. The possible antagonisum was expressed by comparing the contractions brought about by the CCK8 before and after contact with the product to be tested. The product of Example 9, at a dose of $10^{-6}$M presented significant antagonistic activity.

Various modifications of the compounds and method of the invention may be made without departing from the spirit or scope thereof and it should be understood that the invention is intended to be limited only as defined in the appended claims.

What we claim is:

1. All possible isomeric forms and mixtures thereof of compounds of the formula

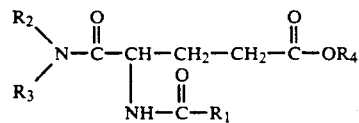

wherein R$_1$ is indolyl, R$_2$ is selected from the group consisting of

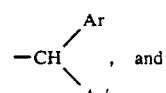
(a)

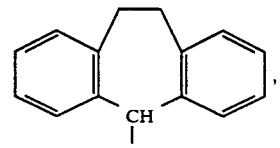
(b)

Ar and Ar' are indolyl, and R$_3$ is hydrogen or R$_2$ and R$_3$ together with the nitrogen to which they are attached form a 5 to 7 member hydrocarbonyl ring optionally containing an oxygen or a second nitrogen unsubstituted or substituted with at least one member of the group consisting of alkyl of 1 to 8 carbon atoms, aryl of 6 to 14 carbon atoms and

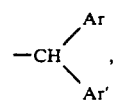

Ar and Ar' having the above definitions and R$_4$ is selected from the group consisting of hydrogen, alkyl of 1 to 8 carbon atoms, cycloalkyl of 3 to 8 carbon atoms,

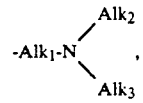

and aralkyl of 7 to 18 carbon atoms unsubstituted or substituted with at least one member of the group consisting of halogen, alkyl and alkoxy of 1 to 8 carbon atoms, dialkylamino with alkyls of 1 to 8 carbon atoms, —CF$_3$, —CN and —NO$_2$, Alk$_1$ is an alkylene of 2 to 8 carbon atoms and Alk$_2$ and Alk$_3$ are individually alkyl of 1 to 8 carbon atoms or cycloalkyl of 3 to 8 carbon atoms.

2. A compound of claim 1 wherein R$_2$ is

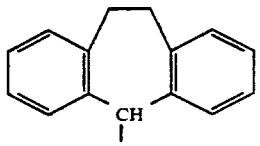

3. A compound of claim 1 wherein R4 is hydrogen.
4. A compound of claim 1 with S configuration at the 4-carbon.
5. A compound of claim 1 selected from the group consisting of (S)-4-[[(1H-indol-2-yl)-carbonyl]-amino]-5-[[bis-(4-methylphenyl)-methyl]-amino]-5-oxo pentanoic acid, (S)-4-[[1H-indol-2-yl)-carbonyl]-amino]-5-[(2-methoxyphenyl)-phenyl-methylamino]-5-oxo pentanoic acid, (S)-5-[[bis-(4-chlorophenyl)-methyl]-amino]-5-oxo-4-[[(1H-indol-2-yl)-carbonyl]-amino]-pentanoic acid and (S)-5-[(10,11-dihydrodibenzo-[a,d]-cyclohepten-5-yl)-amino]-4-[[(1H-indol-2-yl)-carbonyl]-amino]-5-oxo pentanoic acid.
6. A cholecyostokinin agonistic composition comprising a cholecyostokinin agonistically effective amount of at least one compound of claim 1 and an inert pharmaceutical carrier.
7. A composition of claim 6 wherein R2 is

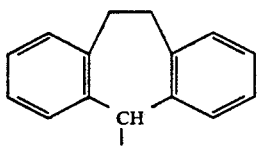

8. A composition of claim 6 wherein R4 is hydrogen.
9. A composition of claim 6 with S configuration at the 4-carbon.
10. A composition of claim 6 wherein the active compound is selected from the group consisting of (S)-4-[[(1H-indol-2-yl)-carbonyl]-amino]-5-[[bis-(4-methylphenyl)-methyl]-amino]-5-oxo pentanoic acid, (S)-4-[[1H-indol-2-yl)-carbonyl]-amino]-5-[(2-methoxyphenyl)-phenyl-methylamino]-5-oxo pentanoic acid, (S)-5-[[bis-(4-chlorophenyl)-methyl]-amino]-5-oxo-4-[[(1H-indol-2-yl)-carbonyl]-amino]-pentanoic acid and (S)-5-[(10,11-dihydrodibenzo-[a,d]-cyclohepten-5-yl)-amino]-4-[[(1H-indol-2-yl)-carbonyl]-amino]-5-oxo pentanoic acid.
11. A method of inducing cholecyostokinin agonistic activity in warm-blooded animals comprising administering to warm-blooded animals a cholecyostokinin agonistically effective amount of at least one compound of claim 1.
12. A method of claim 11 wherein in the active compound R2 is

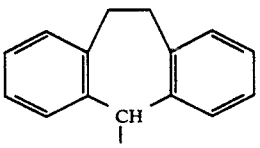

13. A method of claim 11 wherein in the active compound R4 is hydrogen.
14. A method of claim 11 with S configuration at the 4-carbon of the active compound.
15. A method of claim 11 wherein the active compound is selected from the group consisting of (S)-4-[[(1H-indol-2-yl)-carbonyl]-amino]-5-[[bis-(4-methylphenyl)-methyl]-amino]-5-oxo pentanoic acid, (S)-4-[[1H-indol-2-yl)carbony]-amino]-5-[(2-methoxyphenyl)-phenyl-methyl-amino]-5-oxo pentanoic acid, (S)-5-[[bis-(4-chlorophenyl)-methyl]-amino]-5-oxo-4-[[(1H-indol-2-yl)-carbonyl]-amino]-pent-anoic acid and (S)-5-[(10,11-dihydrodibenzo-[a,d]-cyclohepten-5-yl)-amino]-4-[[(1H-indol-2-yl)-carbonyl]-amino]-5-oxo-pentanoic acid.

* * * * *